Figure 3:
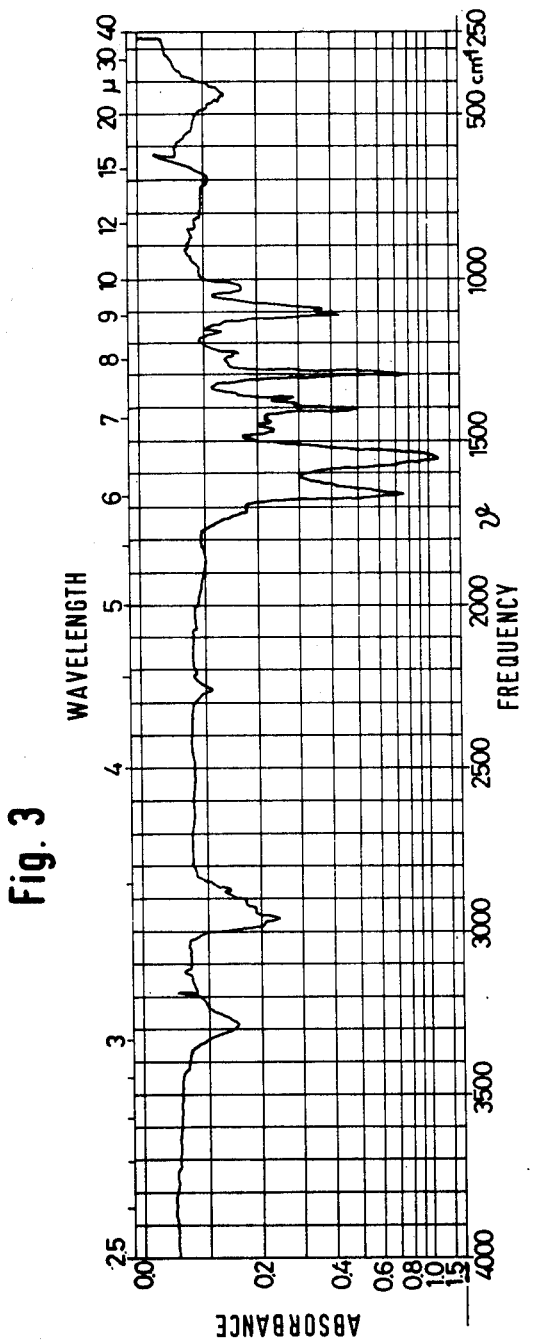

United States Patent [19]

Dalibor

[11] 4,068,086
[45] Jan. 10, 1978

[54] BLOCKED POLYISOCYANATES OBTAINED FROM 2,2,4-TRIMETHYLHEXAMETHYLENE-DIISOCYANATE AND ACETOACETIC ACID ALKYL ESTERS

[75] Inventor: Horst Dalibor, Hamburg, Germany

[73] Assignee: Hoechst Aktiengesellschaft, Frankfurt am Main, Germany

[21] Appl. No.: 669,813

[22] Filed: Mar. 24, 1976

[30] Foreign Application Priority Data

Mar. 25, 1975  Switzerland .......................... 3769/75
Dec. 1, 1975   Switzerland ........................ 15537/75
Mar. 3, 1976   Switzerland .......................... 2628/75

[51] Int. Cl.² .................. C07C 101/24; C07C 101/26
[52] U.S. Cl. ............................ 560/169; 117/161 UC; 428/334
[58] Field of Search ......................... 260/482 R, 482 P

[56] References Cited

PUBLICATIONS

Houben-Weyl "Methoden der Organischen Chemie", vol. 14/2, pp. 61–70, Nov. 4, 1962.

S. Petersen, Annulen, 562, p. 225, (1949).

*Primary Examiner*—Donald G. Daus
*Assistant Examiner*—Lisa Jones
*Attorney, Agent, or Firm*—Gordon W. Hueschen

[57] ABSTRACT

The subject of the invention are completely or partially blocked diisocyanates of the following formula (III)

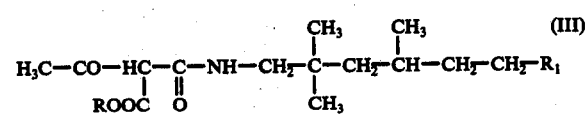

wherein $R_1$ denotes the radical

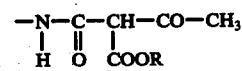

or NCO and R denotes the methyl, ethyl, propyl, isopropyl, n-butyl, tert.-butyl, iso-butyl, sec.-butyl, pentyl, hexyl, heptyl, octyl, nonyl, decyl and dodecyl radical.

2 Claims, 28 Drawing Figures

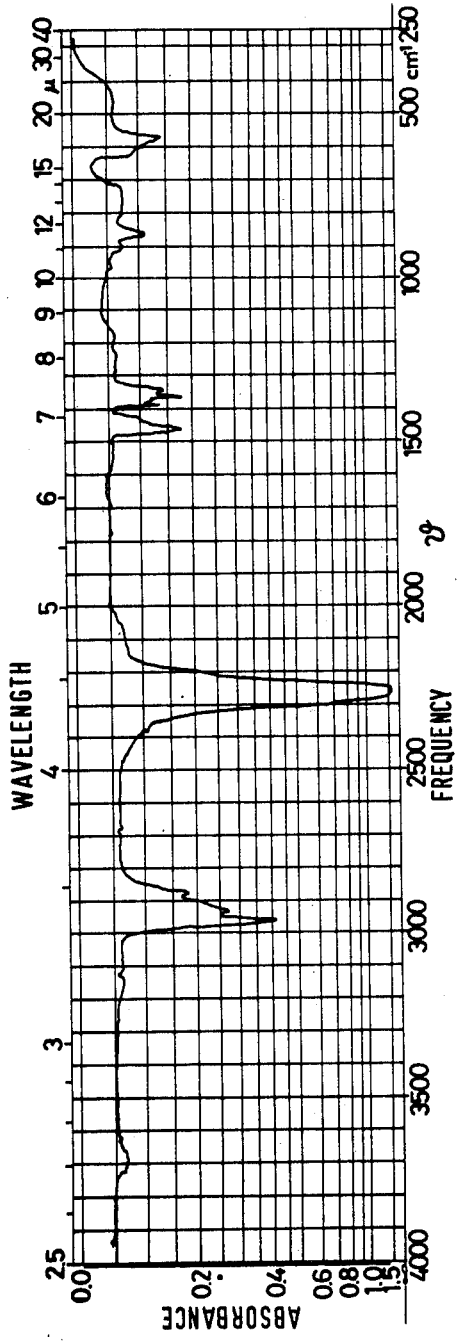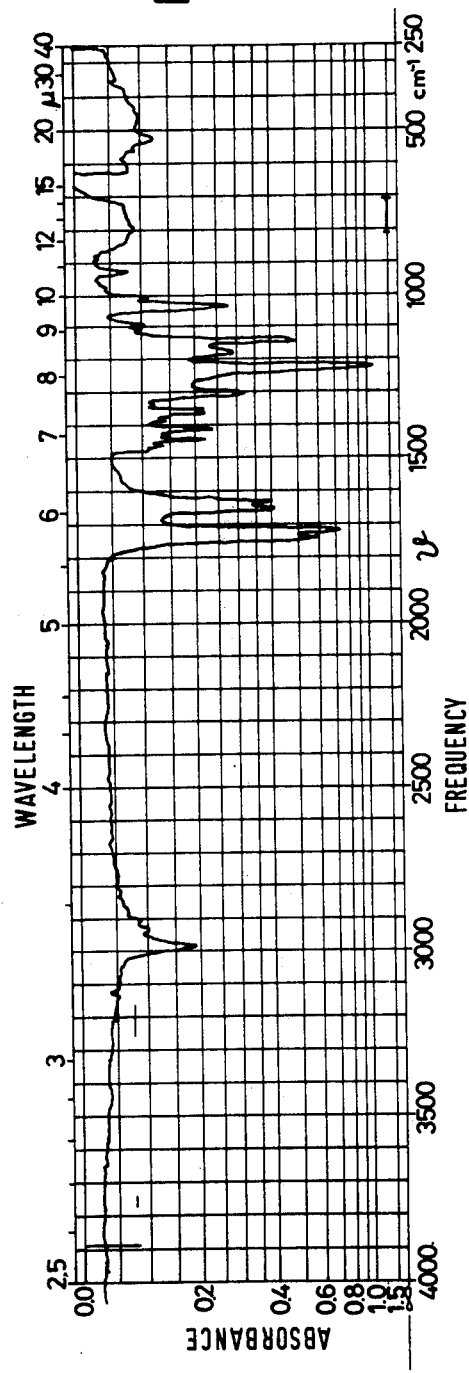

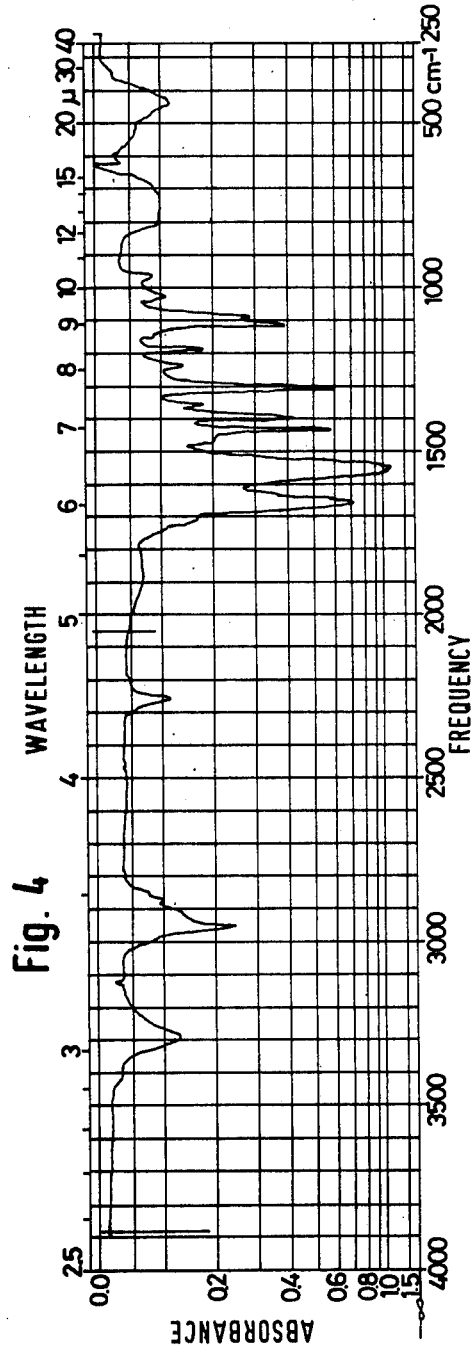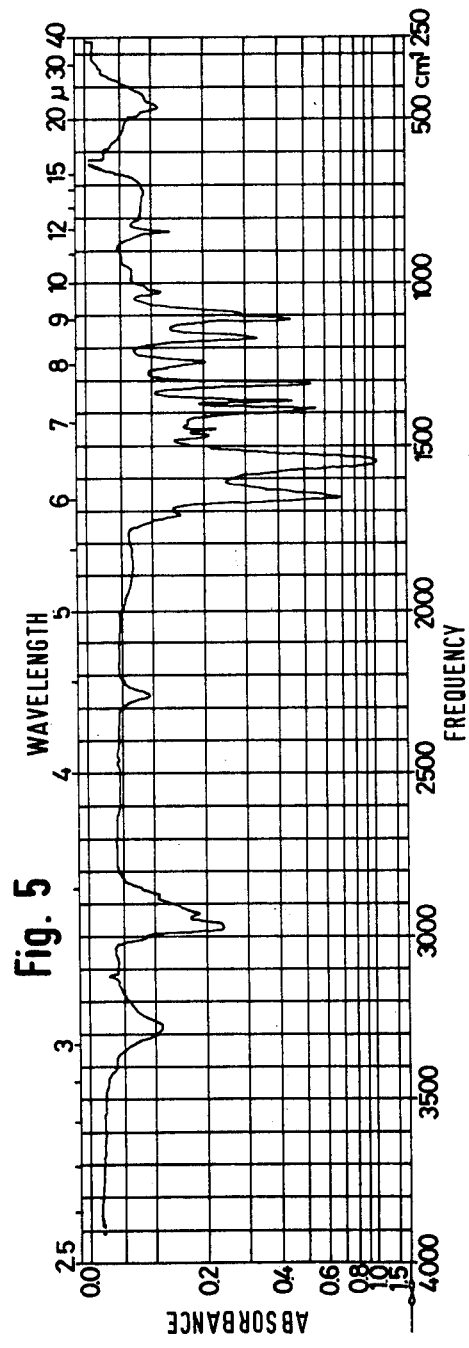

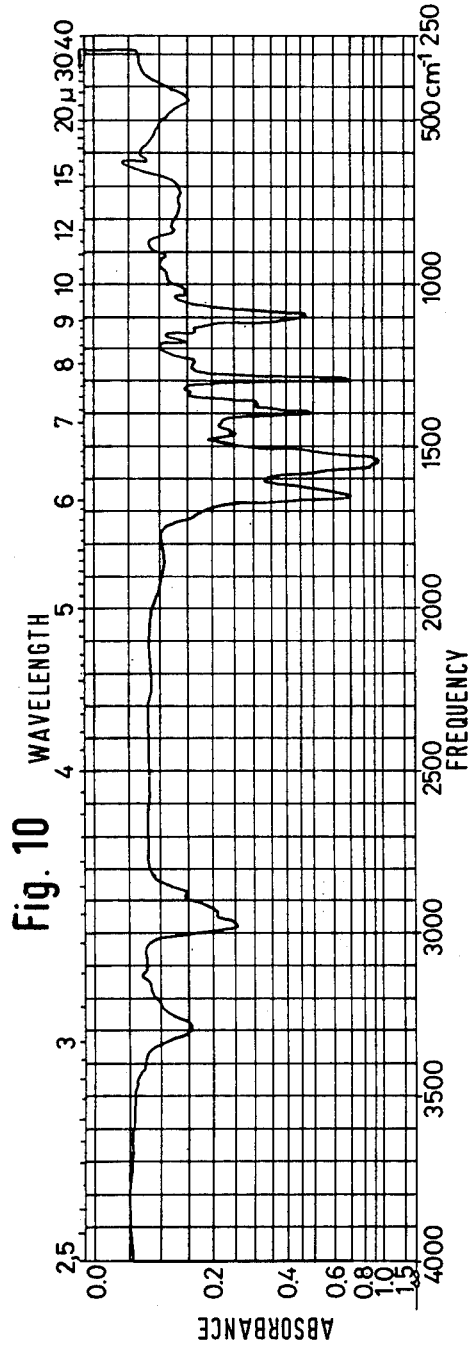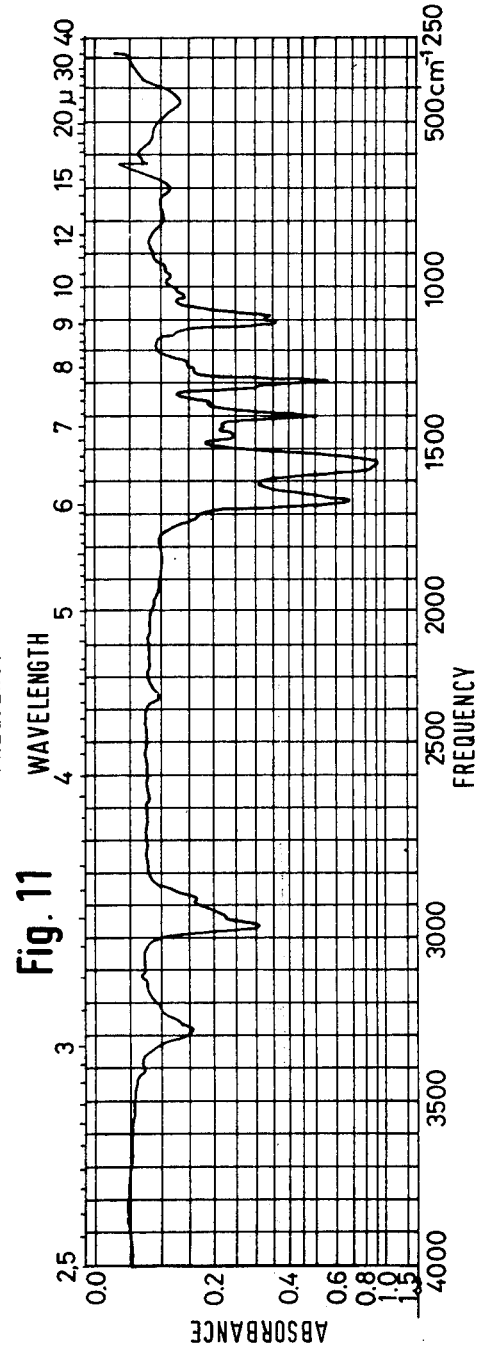

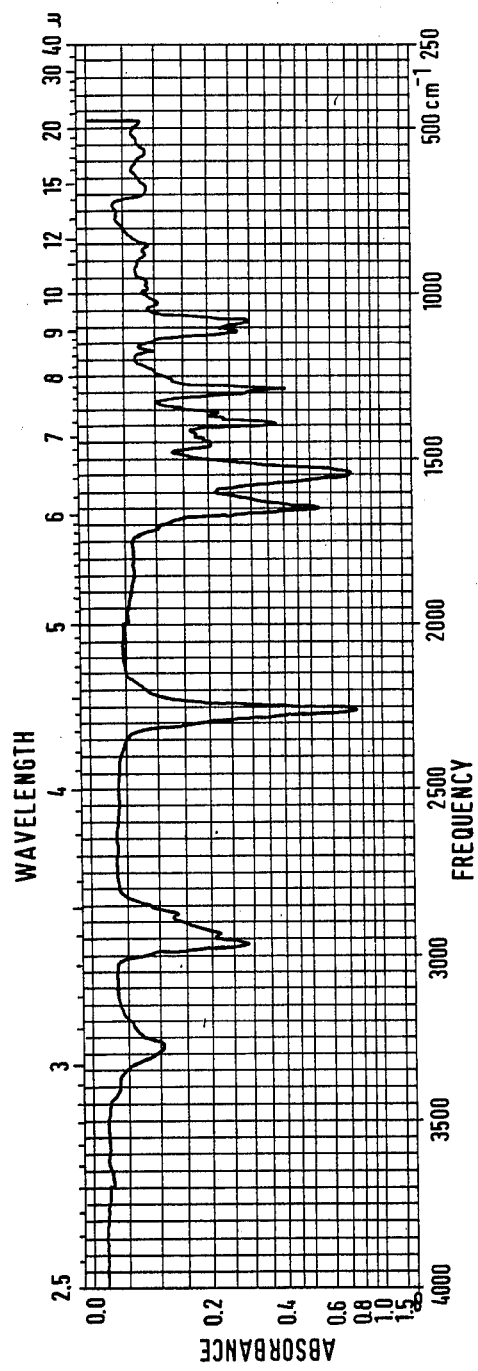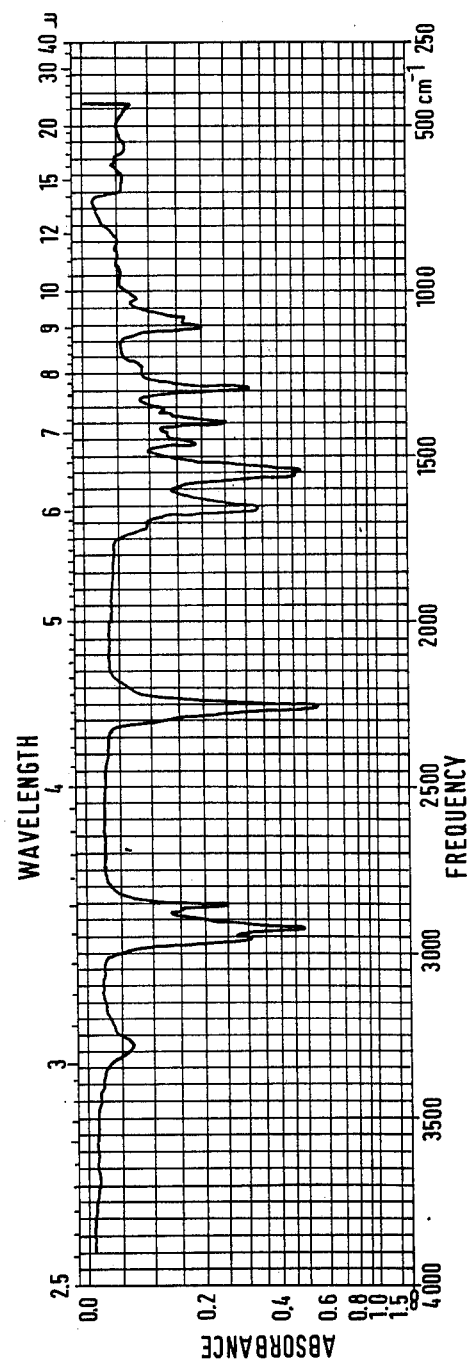

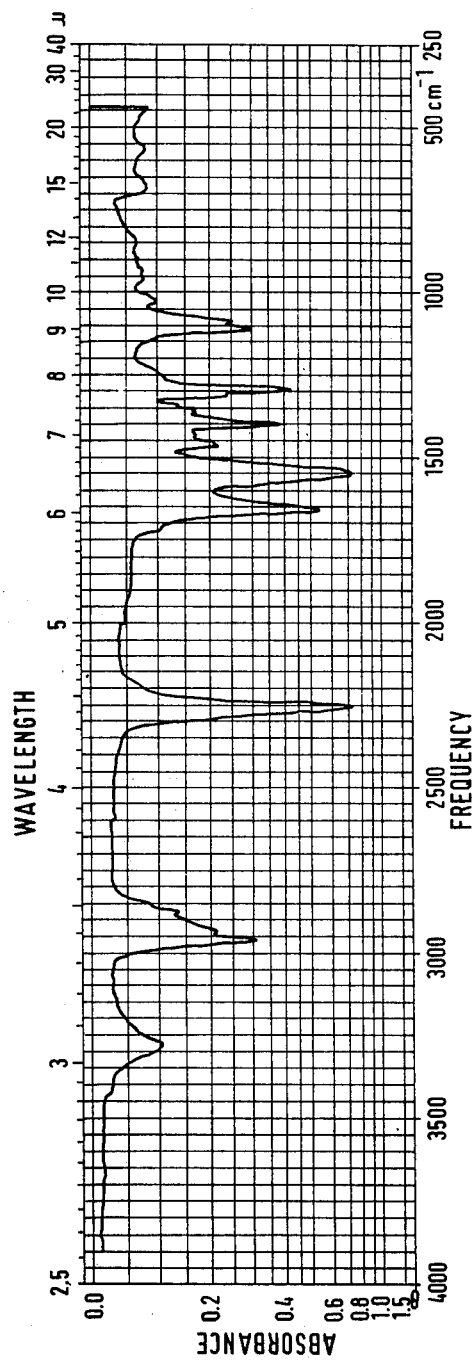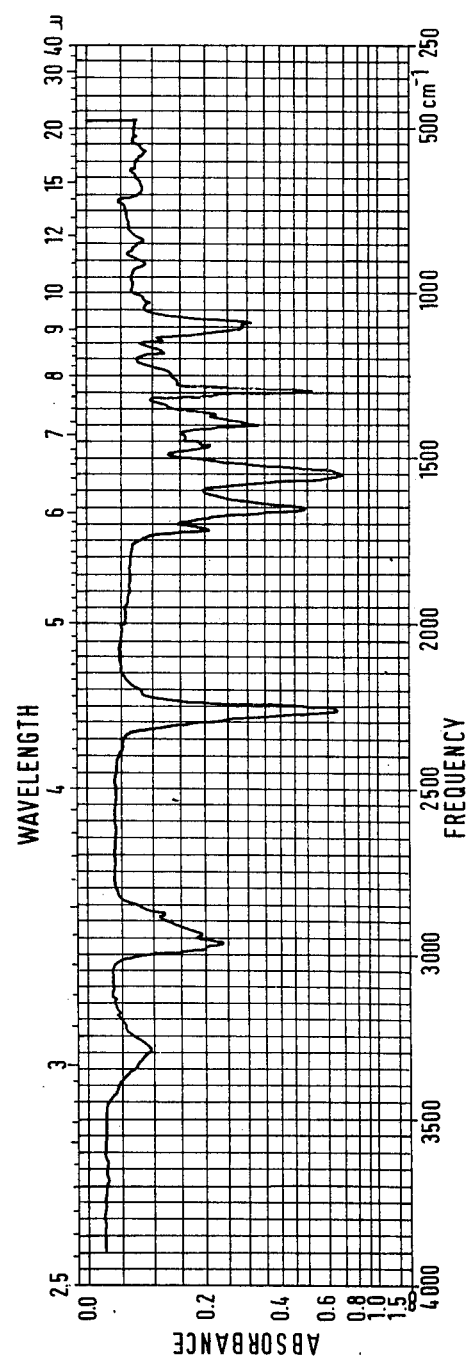

BLOCKED POLYISOCYANATES OBTAINED FROM 2,2,4-TRIMETHYLHEXAMETHYLENE-DIISOCYANATE AND ACETOACETIC ACID ALKYL ESTERS

BACKGROUND OF THE INVENTION

1. Field of the Invention

The manufacture of blocked or masked polyisocyanates is known and is described in Houben-Weyl "Methoden der organischen Chemie" ("Methods of Organic Chemistry"), Volume 14/2, page 61–70.

Reaction products of hexamethylene-1,6-diisocyanate with tert.-butanol, phenol, acetoacetic acid ethyl ester, malonic acid esters, acetylacetone, phthalimide, imidazole, hydrogen chloride, hydrogen cyanide and caprolactam are known.

The above aliphatic isocyanate was reacted with compounds which at elevated temperature split off again, with liberation of the isocyanate group. Such products are described as isocyanate-eliminating compounds or "moderators". In contrast to the free diisocyanates, it is possible to mix such masked diisocyanates with substances or solvents containing hydroxyl groups, without a reaction taking place. It is thus possible, using masked polyisocyanates, to prepare storageable mixtures with products containing hydroxyl groups, such as higher-molecular polyesters or polyethers, which only give the desired isocyanate reactions at an elevated temperature. The masked polyisocyanates are of great importance both for the manufacture of rubbery-elastic products via intermediates which can be stored, and for the manufacture of wire lacquers, as well as in the textile field. The effect of eliminating the isocyanate results from the fact that practically all adducts formed from isocyanates at a moderately elevated temperature again decompose at higher temperatures, equilibria being set up. The setting up of these equilibria is accelerated by addition of tertiary bases.

2. Prior Art

Many of these masked polyisocyanates show unsatisfactory crosslinking at low stoving temperatures when used in combination with polymers containing hydroxyl groups. However, masked isocyanates which decompose again at lower temperatures, given decomposition products which, because of their toxicity, must not be used for stoving lacquers.

A known adduct, manufactured from hexamethylenediisocyanate and acetoacetic acid ethyl ester admittedly does not give any decomposition products which are particularly toxic, and also decomposes again at a low stoving temperature. The known adduct has a melting point of 81° – 82° C and therefore must be prepared in the melt above the melting point, say at about 90° C, which results in an undesirable yellow coloration, which can only be removed by recrystallisation. This solid adduct tends to crystallise and results in an undesirable inhomogeneity of the lacquer solutions prepared therewith. Thus, for example, when combining polymers, containing hydroxyl groups, with the known adduct, the stoved lacquers have greatly worsened film properties.

It is the object of the invention to provide completely or partially blocked diisocyanates which at room temperature are in the form of a liquid and are soluble in inert solvents customary in the lacquer industry.

It is a further object of the present invention to provide blocked liquid polyisocyanates which in a temperature range of 80° – 130° C, preferably 90° – 130° C, in the presence of polymers containing hydroxyl groups, give crosslinked reaction products.

SUMMARY

The subject of the invention are completely or partially blocked diisocyanates of the following formula (III)

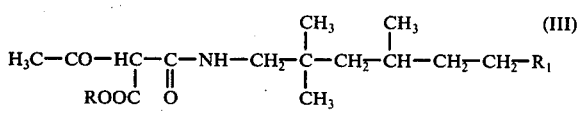

wherein $R_1$ denotes the radical

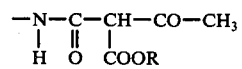

or NCO and R denotes the methyl, ethyl, propyl, isopropyl, n-butyl, tert.-butyl, iso-butyl, sec.-butyl, pentyl, hexyl, heptyl, octyl, nonyl, decyl and dodecyl radical.

The pentyl radical may be present in 8 isomeric forms (apart from optical antipodes), and these may be present individually or as mixtures. The starting material, pentanol, for the manufacture of the acetoacetic acid pentyl ester which is reacted with the polyisocyanate can be, for example, a commercially available fusel oil or an amyl alcohol obtained by fermentation, 1-pentanol (n-amyl alcohol, n-butylcarbinol), $H_3C-(CH_2)_3-CH_2OH$; 2-pentanol (sec.-amyl alcohol, methylpropylcarbinol), $CH_3-(CH_2)_2-CHOH-CH_3$; 3-pentanol (diethylcarbinol), $CH_3-CH_2-CHOH-CH_2-CH_3$; primary and secondary isoamyl alcohols (3-methyl-1-butanol and 3-methyl-2-butanol respectively), $(CH_3)_2CH-CH_2-CH_2OH$ and $(CH_3)_2CH-CHOH-CH_3$ respectively; 2-methyl-1-butanol, 2,2-dimethyl-1-propanol and tert.-amyl alcohol (2-methyl-2-butanol).

The hexyl radical is present as the 1-hexyl radical and/or in 16 isomeric forms. The corresponding hexanols which can be used for the manufacture of the acetoacetic acid hexyl ester are described in BEILSTEIN E III, 1: 1,650, and amongst them those which are liquid at room temperature are preferred.

The appropriate heptyl alcohols and their isomers, which can be used for the manufacture of the acetoacetic acid heptyl ester, are described in BEILSTEIN E III, 1: 1,679 – 1,687, and amongst them those which are liquid at room temperature are preferred.

The appropriate octyl alcohols and their isomers, which can be used for the manufacture of the acetoacetic acid octyl ester, are described in BEILSTEIN E IV, 1: 1,756, 1,770 and 1,779, and amongst them those which are liquid at room temperature are preferred.

The appropriate nonyl alcohols and their isomers, which can be used for the manufacture of the acetoacetic acid nonyl ester, are described in BEILSTEIN E IV, 1: 1,798, 1,803 and 1,804, and amongst them those which are liquid at room temperature are preferred.

The appropriate decyl alcohols and their isomers, which can be used for the manufacture of the acetoacetic acid decyl ester, are described in BEILSTEIN E III, 1: 1,758, and amongst them those which are liquid at room temperature are preferred.

The appropriate dodecyl alcohols and their isomers, which can be used for the manufacture of the acetoacetic acid dodecyl ester, are described in BEILSTEIN E III, 1: 1,781, and amongst them those which are liquid at room temperature are preferred.

The new completely or partially blocked diisocyanates of the formula III are manufactured by reaction of an acetoacetic acid alkyl ester, in which the alkyl radical is R, with 2,2,4-trimethylhexamethylenediisocyanate, at elevated temperature.

A further subject of the invention is a process for the manufacture of a blocked diisocyanate of the formula I

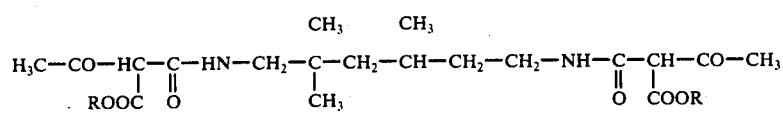 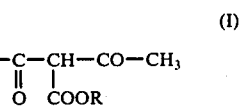   (I)

wherein R denotes the methyl, ethyl, propyl, iso-propyl, n-butyl, tert.-butyl, iso-butyl, sec.-butyl, pentyl, hexyl, heptyl, octyl, nonyl, decyl and dodecyl radical, characterised in that an acetoacetic acid alkyl ester, in which the alkyl radical is R, is reacted with 2,2,4-trimethylhexamethylenediisocyanate in the molar ratio of 2.0 to 2.1: 1, whilst warming, in the presence of a catalyst.

The subject of the invention is likewise a process for the manufacture of partially blocked diisocyanate of the formula (II)

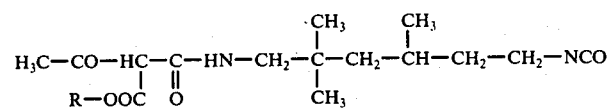   (II)

wherein R denotes the methyl, ethyl, propyl, iso-propyl, n-butyl, tert.-butyl, iso-butyl, sec.-butyl, pentyl, hexyl, heptyl, octyl, nonyl, decyl and dodecyl radical, characterised in that an acetoacetic acid alkyl ester, in which the alkyl radical is R, is reacted with 2,2,4-trimethylhexamethylenediisocyanate in the molar ratio of 1.0 to 1.05: 1, whilst warming, in the presence of a catalyst.

For the manufacture of the new compounds of the formula (I) the reaction is carried out at 60° to 120° C, preferentially at 70° to 100° C. There is needed a reaction time of 3 to 20 hours. As the reaction goes exothermically, if the reaction members are inserted as a mixture, preferably no mixture is inserted, which contains the two partners from the very beginning in an equivalent ratio. Preferably the acetoacetic acid alkyl ester and the catalyst are filled in the reaction vessel and heated to the desired reaction temperature and kept at this temperature. After the reaction temperature has reached, 2,2,4-trimethylhexamethylenediisocyanate is added gradually in the course of several hours. Then the mixture is kept at reaction temperature as long as the reaction has finished practically at least 95%. After cooling to room temperature, the not yet transformed reaction members go on reacting, so that the reaction is to be looked as completed after maximal 3 weeks of storage time.

A preferred execution form of the process for the manufacture of the new compounds of the formula (II) is characterised in that the 2,2,4-trimethylhexamethylenediisocyanate and the catalyst are heated to about 60° to 90° C in the reaction vessel and the necessary amount of acetoacetic acid alkyl ester is added gradually in the course of 1 to 3 hours by keeping the said temperature, and then the reaction temperature is kept as long as the reaction product of the formula (II) is obtained.

As raw product the obtained reaction products are relatively very light, weakly yellowish liquids which can be used in the lacquer and synthetic resin industry without further chemical procedure. The raw reaction products are a liquid, at all events, at 10° to 80° C.

The particular advantage of the new compounds is that they can be prepared as a liquid by reaction of the components in the presence of catalysts and in the absence of solvents, at low temperatures, between about 60° to 120° C, preferably 70° to 100° C, and that the reaction products are still liquid even at 0° C.

Catalysts which can be used are sodium, sodium ethylate and zinc acetylacetonate. The latter is particularly advantageous since it gives products completely free from turbidity.

Using this process, the reaction products are furthermore obtained with the desired low viscosities.

These new compounds are distinguished by very special technological properties. They do not suffer from the disadvantages of the previously known blocked polyisocyanates, which have been described. Lacquer combinations of copolymers, containing hydroxyl groups, based on hydroxyalkyl esters of acrylic acid or methacrylic acid and esters of acrylic acid or methacrylic acid crosslink with the new completely blocked polyisocyanate under the conditions of a conversion of masked NCO : OH = from 0.5 to 1 : 1 at 80° to 130° C, and give very resistant lacquerings.

Because of the low viscosity of the new completely or partially blocked diisocyanate, it is possible, using the binder combination with copolymers containing hydroxyl groups, as described above, to achieve high solids contents in the ready-to-spray stable lacquer solutions, which give lacquers of low solvent content and thus take into account the requirements of protection of the environment.

The new completely or partially blocked diisocyanates of the present invention can be used, quite generally, for all purposes in lacquer chemistry and plastics chemistry in which completely or partially blocked diisocyanates have already been used successfully.

The following may be mentioned as examples of polyhydroxylic polymers or hydroxylic synthetic resins which can be crosslinked on heating with the masked diisocyanates according to the invention: saturated polyester resins, unsaturated polyester resins, saturated or unsaturated oil-modified or fatty acid-modified alkyd resins, phenol-formaldehyde resols, aminoplast resins, polyurethane resins, polyethers, epoxide resins, cellulose acetobutyrate and copolymers containing hydroxyl groups.

Polyester resins which can be used are those which contain co-condensed aliphatic and aromatic dicarboxylic acids with 4 to 12 carbon atoms and polyols with 2 to 10 carbon atoms and 2 to 4 primary or secondary hydroxyl groups. Such saturated and unsaturated polyester resins are described in Houben-Weyl "Makromolekulare Stoffe II" ("Macromolecular Substances II"), Volume 14/2, page 4 to 42.

As oil-modified or fatty acid-modified alkyd resins, it is possible to use those which contain, in a co-condensed form, 10 to 50% by weight of saturated or unsaturated aliphatic fatty acids with 8 to 18 carbon atoms, dicarboxylic acids with 4 to 12 carbon atoms and polyols with 2 to 10 carbon atoms and 2 to 4 primary or secondary hydroxyl groups, such as are described in Wagner/Sarx "Lackkunstharze" ("Synthetic Resins for Lacquers"), 5th Edition, page 99 to 123.

The phenol-resols used are those described in Houben-Weyl "Makromolekulare Stoffe II" ("Macromolecular Substances II"), Volume 14/2, page 220 to 230.

The aminoplast resins which can be used are those described in Wagner/Sarx "Lackkunstharze" ("Synthetic Resins for Lacquers"), 5th Edition, page 61 to 80.

The epoxide resins used are those which are obtained by reaction of bisphenol A and epichlorohydrin in an alkaline medium. Such resins have epoxide equivalents of 450 to 4,000 and Durran softening points of 65° to 155° C. Such epoxide resins are described in Houben-Weyl "Makromolekulare Stoffe II" ("Macromolecular Substances II"), Volume 14/2, page 468 to 475.

The cellulose esters with 1 to 4 carbon atoms in the ester radical, which are employed, are those which have a butyryl content of 17 to 55% by weight, an acetyl content of 2 to 40% by weight and a hydroxyl content of 0.5 to 5% by weight. Mixed fatty acid esters of cellulose are described in Houben-Weyl "Makromolekulare Stoffe II" ("Macromolecular Substances II"), Volume 14/2, page 877 to 879.

Copolymers used are those which contain copolymerised acrylic acid esters or methacrylic acid esters with 1 to 8 carbon atoms in the alkyl radical, hydroxyalkyl acrylate and/or hydroxyalkyl methacrylates and optionally also other polymerisable monomers, the products having hydroxyl numbers of 33 to 300. Such copolymers are described in the book Wagner/Sarx "Lackkunstharze" ("Synthetic Resins for Lacquers"), 5th Edition (1971), page 230 to 235.

The constituents are mixed in the ratio of 5 to 50% by weight of the reaction products, according to the invention, of 2,2,4-trimethylhexamethylenediisocyanate and acetoacetic acid alkyl esters and 50 to 95% by weight of the synthetic resins containing hydroxyl groups. The ratio in which they are mixed further has to conform to the fact that for one hydroxyl group 0.3 to 1.2 NCO groups, in the form of blocked isocyanate groups, are employed.

Table 1 which follows illustrates exemplarily the synthetic resins 1 to 10, containing hydroxyl groups, which are used for the stoving coatings.

In the following Table 2 the results of examination of coatings manufactured with stoved lacquers are shown. Hereby the synthetic resins mentioned in Table 1 and those completely masked diisocyanates obtained according to the Examples 3, 4 and 5 were used.

These informing investigations show that the products of this invention are to be utilized industrially in many respects. The good transparency of films is to be emphasized. This means that the components contained in the lacquer do not show any signs of incompatibility after stoving. Moreover, the stoved films show a high gloss, a good surface hardness as follows from the proof of pendulum hardness. The stoved films show a high elasticity and have a good resistance against organic solvents. The stoved films do not present any yellowing, except the stoved lacquers, based on phenol-resols, always showing a yellowing.

By the results as shown in Table 3 it is proved that the masked diisocyanates of this invention in dependence of the alkyl radical of the acetoacetic acid alkyl esters are differently reactive by decomposing again in the warmth. At a stoving time of 30 to 40 minutes, the desired crosslink of the stoved lacquer coating already happens at 90° – 100° C, if the diisocyanate is masked with the acetoacetic acid-tert.-butylester or the acetoacetic acid-tert.-amylester. As far as the diisocyanate is masked with other acetoacetic acid alkyl esters, containing no tertiary carbon atoms in the alkyl radical, the crosslink in the stoving lacquers happens at the same stoving time (30 to 40 minutes) at 110° – 130° C. The results of measurement in Table 3 show that the completely masked diisocyanate obtained according to Example 4 with the indicated copolymers gives excellent films at the stoving temperatures between 90° to 120° C, whereas the completely masked diisocyanate obtained according to Example 3 with the same copolymer requests temperatures of about 110° to 120° C in order to give good films.

Moreover, the products of the polyisocyanate-acetoacetic acid alkyl ester adducts according to the invention are preferably suitable for the improvement of lacquer coatings consisting of resins, not being crosslinked in themselves with isocyanates, containing, however, groups capable of reaction in connection with isocyanates, resins, such as alkyd resins and polyacrylates. To such coatings they give high gloss, high flexibility as well as improved resistance to solvents and weather.

The lacquer solutions and coatings produced by using the polyisocyanate-acetoacetic acid alkyl ester adducts according to the invention can contain the pigments and additives as commonly used in the lacquer industry.

Table 1

| Synthetic resins | Composition of the synthetic resins for use with the reaction products, according to the invention, of 2,2,4-trimethylhexamethylenediisocyanate and acetoacetic acid alkyl esters |
|---|---|
| 1 | Epoxide resin, based on bisphenol A and epichlorohydrin with an epoxide equivalent weight of 875 to 1000, described in Hoechst Company brochure Beckopox EP 304 |
| 2 | Epoxide resin, based on bisphenol A and epichlorohydrin with an epoxide equivalent weight of 450 to 505, described in Hoechst Company brochure Beckopox EP 301 |
| 3 | Phenol-resol, reaction product of phenol and formaldehyde, condensed in an alkaline medium in the ratio of 1 : 1.5, described in Hoechst Company brochure Phenodur PR 101 |
| 4 | Non-plasticised melamine formaldehyde resin, 55% strength solution in xylene/butanol, density of 1.008 at 20° C, described in Casella Company brochure Maprenal TTX |
| 5 | Ricinenic oil alkyd resin, with an oil content of 35% and a phthalic anhydride content of 40%, described in Hoechst Company brochure Alftalat AR 351 |
| 6 | Coconut oil alkyd resin with an oil content of 35% and a phthalic anhydride content of 45%, described in Hoechst Company brochure Alftalat AC 350 |
| 7 | Cellulose acetobutyrate, described in Eastman Chemical Company brochure EAB 531/1 |
| 8 | Unsaturated polyesters, consisting of 0.5 mol of maleic anhydride, 4.5 mols of phthalic anhydride and 6 mols of neopentylglycol. The viscosity of a 70% strength solution in ethylglycol acetate is X-Y, |

Table 1-continued 9. measured on the Gardner-Holdt scale. The acid number has a value of 15.
Saturated polyesters, consisting of 3 mols of phthalic anhydride and 3 mols of trimethylolpropane. The viscosity of a 50% strength solution in ethylglycol acetate is V-W, measured on the Gardner-Holdt scale. The acid number has a value of 12.

10. Copolymer solution, consisting of 20% by weight of styrene, 20% by weight of hydroxyethyl methacrylate, 30% by weight of methyl methacrylate, 30% by weight of 2-ethylhexyl acrylate and 100% by weight of xylene. The viscosity of the 50% strength solution in xylene is U, measured on the Gardner-Holdt scale. The hydroxyl number has a value of 80.

Table 2

Stoved coatings obtained from synthetic resins containing hydroxyl groups and the reaction products, according to the invention, of 2,2,4-trimethylhexamethylenediisocyanate and acetoacetic acid alkyl esters.

| Used synthetic resin acc. to Table 1 | 1 | 2 | 3 | 4 | 5 | 6 | 7 | 8 | 9 | 10 | 10 | 10 |
|---|---|---|---|---|---|---|---|---|---|---|---|---|
|  | 70% by weight | 70% by weight | 70% by weight | 70% by weight | 80% by weight | 80% by weight | 80% by weight | 80% by weight | 65% by weight | 80% by weight | 80% by weight | 80% by weight |
| Example 3 according to the invention | 30% by weight | 30% by weight | 30% by weight | 30% by weight | 20% by weight | 20% by weight | 20% by weight | 20% by weight | 35% by weight | 20% by weight | | |
| Example 4 according to the invention | | | | | | | | | | | 20% by weight | |
| Example 5 according to the invention | | | | | | | | | | | | 20% by weight |
| Stoving temperature 130° C. 40 minutes | | | | | | | | | | | | |
| Film transparency | 1 | 1 | | 1 | 1 | 1 | | 1 | 1 | 1 | 1 | 1 |
| Gloss | 1 | 1 | | 1 | 1 | 1 | | 1 | 1 | 1 | 1 | 1 |
| Yellowing | 1 | 1 | | 1 | 1 | 1 | | 1 | 1 | 1 | 1 | 1 |
| Konig pendulum hardness | 247 secs. | 240 secs. | | 218 secs. | 110 secs. | 67 secs. | | 214 secs. | 219 secs. | 200 secs. | 198 secs. | 199 secs. |
| Elasticity | 1 | 2 - 3 | | 3 | 1 | 1 | | 3 | 1 | 2 | 1 - 2 | 1 |
| Resistance to xylene, 6 minutes | 3 | 3 - 4 | | 1 | 2 | 3 - 4 | | 4 | 1 | 1 - 2 | 1 - 2 | 2 |
| Stoving temperature 150° C. 40 minutes | | | | | | | | | | | | |
| Film transparency | 1 | 1 | 1 | 1 | 1 | 1 | 1 | 1 | 1 | 1 | 1 | 1 |
| Gloss | 1 | 1 | 2 | 1 | 1 | 1 | 1 | 1 | 1 | 1 | 1 | 1 |
| Yellowing | 1 | 1 | 5 | 1 | 3 | 1 | 1 | 1 | 1 | 1 | 1 | 1 |
| Konig pendulum hardness | 242 secs. | 234 secs. | 244 secs. | 215 secs. | 111 secs. | 64 secs. | 178 secs. | 201 secs. | 221 secs. | 191 secs. | 192 secs. | 191 secs. |
| Elasticity | 1 | 2 - 3 | 1 | 2 | 1 | 1 | 1 - 2 | 3 | 1 | 2 | 2 | 2 |
| Resistance to xylene, 6 minutes | 2 | 3 | 1 | 1 | 2 | 3 - 4 | 3 | 3 - 4 | 1 | 2 | 2 | 2 - 3 |

Assessment of stoved coatings:
1 = best value
5 = worst value

Table 3

Stoved coatings obtained from copolymer containing hydroxyl groups and the reaction products, according to the invention, of 2,2,4-trimethylhexamethylenediisocyanate and acetoacetic acid alkyl esters, with different alkyl radicals in dependence of the stoving temperature.

| used synthetic resin | Example 3 according to the invent. | | | | Example 4 according to the invention | | | |
|---|---|---|---|---|---|---|---|---|
| synth. resin 10 acc. to Table 1 80% by weight copolymer | 20 % by weight of reaction product of 2,2,4-trimethylhexamethylene-diisocyanate and acetoacetic acid alkyl ester | | | | 20 % by weight of reaction product of 2,2,4-trimethylhexamethylenediisocyanate and acetoacetic acid-tert.-butyl ester | | | |
|  | Stoving conditions 40 minutes at | | | | Stoving conditions 40 minutes at | | | |
|  | 90° C | 100° C | 110° C | 120° C | 90° C | 100° C | 110° C | 120° C |
| Konig pendulum hardness in sec. | 60 | 75 | 130 | 180 | 140 | 172 | 174 | 178 |
| Resistance to xylene after one minute | 5 | 4 | 4 | 4 | 2 | 1 | 1 | 1 |
| Resistance to xylene after six minutes | — | 5 | 4 | 2 | 2 - 3 | 1 - 2 | 1 - 2 | 1 - 2 |

Assessment of stoved coatings:
1 = best value
5 = worst value

EXAMPLE 1

265 g of acetoacetic acid ethyl ester and 0.3 g of sodium are heated to 75° C under nitrogen, whilst stirring, and 210 g of 2,2,4-trimethylhexamethylenediisocyanate are uniformly added dropwise over the course of 2 hours whilst maintaining the temperature at 75° C, after which the mixture is kept at 75° C for 1 hour. The NCO content is 0.22. The viscosity is V - W, measured on the Gardner-Holdt scale. The iodine colour number, measured according to DIN Specification 6162 with the Lovibond 1000 Comparator is 7.

Refractive index: $n_D^{22} = 1.5105$.

FIG. 1 shows the infra-red spectrum of the diisocyanate starting material, that is 2,2,4-trimethylhexamethylenediisocyanate, FIG. 2 shows the infra-red spectrum of acetoacetic acid alkyl ester starting material, that is acetoacetic acid ethyl ester, FIG. 3 shows the infra-red spectrum of the reaction product from the starting materials according to FIG. 1 and FIG. 2, obtained according to Example 1.

EXAMPLE 2

265 g of acetoacetic acid ethyl ester and 0.3 g of sodium ethylate are heated to 75° C under nitrogen gas, whilst stirring, 210 g of 2,2,4-trimethylehexamethylenediisocyanate are added dropwise uniformly over the course of two hours at the same temperature, and the mixture is reacted for 8 hours at 75° C. The NCO content is 1.3. The viscosity is L, measured on the Gardner-Holdt scale. The iodine colour number has a value of 4.

Refractive index: $n_D^{22} = 1.5105$.

EXAMPLE 3

265 g of acetoacetic acid ethyl ester and 0.3 g of zinc acetylacetonate are heated to 75° C whilst stirring and introducing nitrogen, 210 g of 2,2,4-trimethylhexamethylenediisocyanate are added uniformly over the course of 2 hours and the reaction is completed over the course of 8 hours at 75° C.

The NCO content is 1.3%. The viscosity is J, measured on the Gardner-Holdt scale. The iodine colour number reaches a value of 1.

Refractive index: $n_D^{22} = 1.5105$.

EXAMPLE 4

324 g of acetoacetic acid tert.-butyl ester and 0.33 g of zinc acetylacetonate are heated to 90° C under nitrogen gas, whilst stirring, and 210 g of 2,2,4-trimethylhexamethylenediisocyanate are uniformly added dropwise over the course of two hours, at the same temperature, and the mixture is reacted for 5 hours at 90° C. The NCO content is 0.9%. The viscosity is $Z_4 - Z_5$, measured on the Gardner-Holdt scale. The iodine colour number has a value of 2 - 3.

Refractive index: $n_D^{22} = 1.4975$.

FIG. 4 shows the infra-red spectrum of the reaction product, obtained according to Example 4.

EXAMPLE 5

238 g of acetoacetic acid methyl ester and 0.3 g of zinc acetylacetonate are heated to 90° whilst stirring and introducing nitrogen, 210 g of 2,2,4-trimethylhexamethylenediisocyanate are added uniformly over the course of 2 hours and the reaction is completed over the course of 5 hours at 90° C.

The NCO content is 1.3%. The viscosity is U, measured on the Gardner-Holdt scale. The iodine colour number reaches a value of 3.

Refractive index: $n_D^{22} = 1.5120$.

FIG. 5 shows the infra-red spectrum, obtained according Example 5.

As shown by the Examples, the blocked diisocyanates manufactured by the process according to the invention have, after manufacture, an NCO content of about 0.2 to 1.3% by weight. Examinations by thin layer chromatography have shown that the products of the process of the present invention are free from the diisocyanate initially employed. The NCO content is attributable to the (mono-masked) reaction product of 1 mol of 2,2,4-trimethylhexamethylenediisocyanate and 1 mol of acetoacetic acid alkyl ester.

On storing the products of the process at room temperature, the masking reaction continues, so that after about 2 to 3 weeks from the day of manufacture, the NCO content is less than 0.1% by weight.

The experimental results shown in Table 2 were obtained by spreading the mixtures, in solvents, on glass plates to give a dry film thickness of 50 to 60 μm.

EXAMPLE 6

Figure 6:
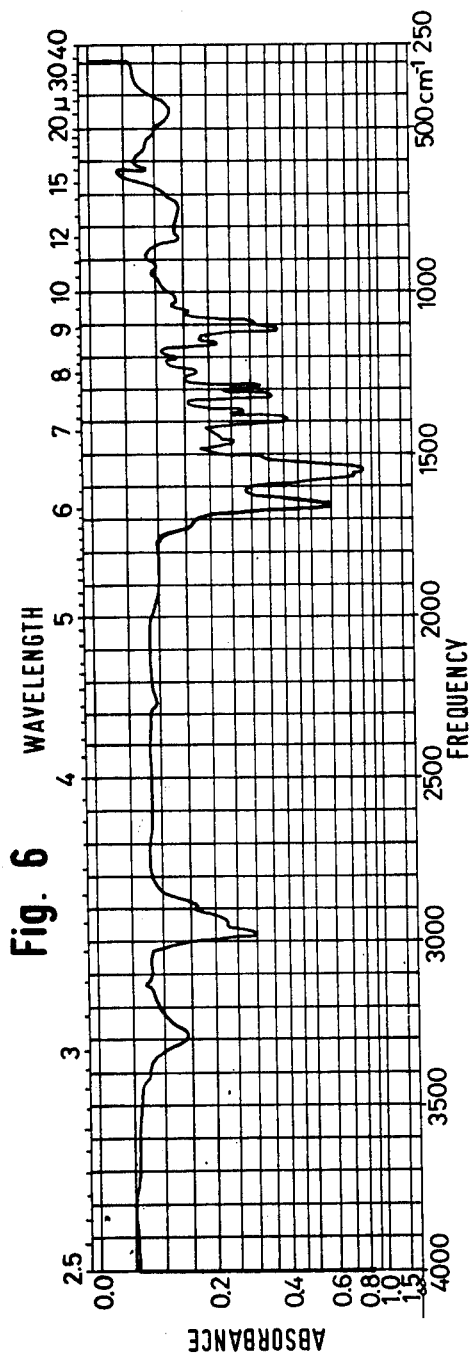

As acetoacetic acid pentyl ester 176 g of acetoacetic acid-tert.-amylester and 0.2 g of zinc acetylacetonate are heated to 95° C whilst stirring and introducing nitrogen, 105 g of 2,2,4-trimethylhexamethylenediisocyanate are uniformly added dropwise over the course of 2 hours whilst maintaining the temperature at 95° C, after which the mixture is kept at 95° C for 4 hours. The NCO content is 1.02. The viscosity is lying at $Z_2$, measured on the Gardner-Holdt scale. The iodine colour number, measured, according to DIN Specification 6162 with the Lovibond 1000 Comparator, is 5. Three weeks after the manufacture, the product had the following properties: refractive index: $n_D^{22} = 1.5010$, the NCO content being 0.3%. FIG. 6 shows the infra-red spectrum, obtained according to Example 6.

EXAMPLE 7

Figure 7:
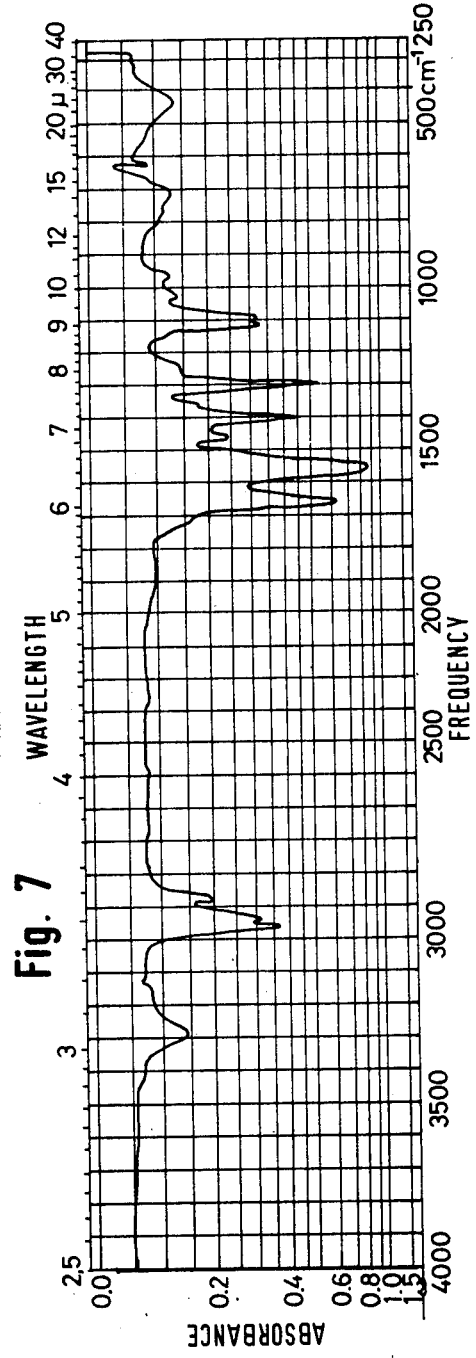

As acetoacetic acid pentyl ester 176 g of acetoacetic acid-n-amylester and 0.2 g of zinc acetylacetonate are heated to 95° C whilst stirring and introducing nitrogen, 105 g of 2,2,4-trimethylhexamethylenediisocyanate are uniformly added dropwise over the course of 2 hours whilst maintaining the temperature at 95° C, then reacted at 95° C for 8 hours. The NCO content is 0.8. The viscosity is H, measured on the Gardner-Holdt scale. The iodine colour number has a value of 6. Three weeks after manufacture, the product had the following properties: refractive index: $n_D^{22} = 1.5017$, the NCO content being 0.2%. FIG. 7 shows the infra-red spectrum, obtained according to Example 7.

EXAMPLE 8

Figure 8:
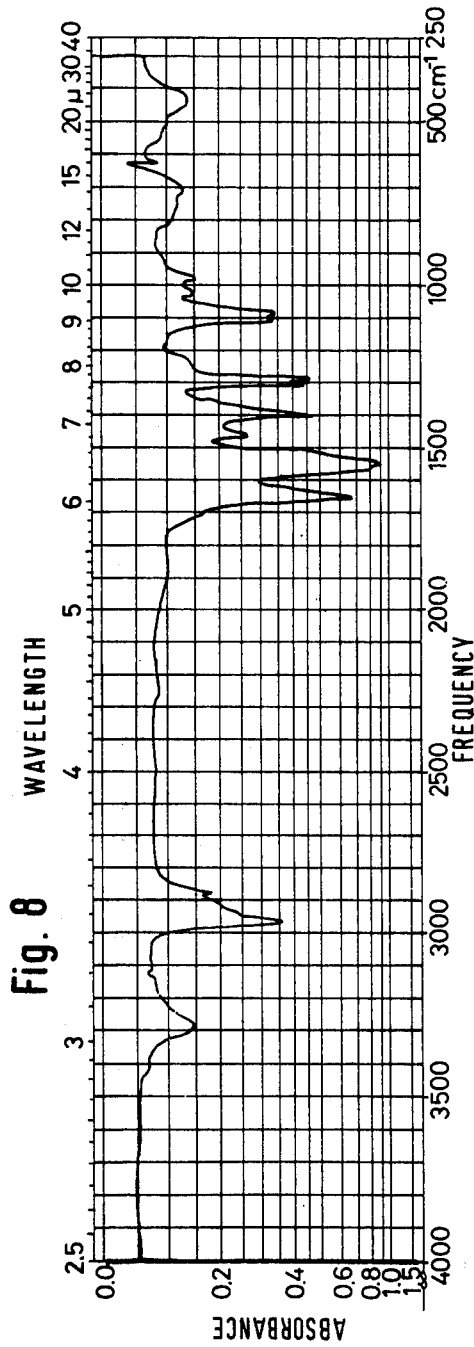

162 g of acetoacetic acid-iso-butylester and 0.18 g of zinc acetylacetonate are heated to 95° C whilst stirring and introducing nitrogen, 105 g of 2,2,4-trimethylhexamethylenediisocyanate are uniformly added over the course of 2 hours and the reaction is carried out in the course of 8 hours at 95° C. The NCO content is 1.1%. The viscosity is U, measured on the Gardner-Holdt scale. The iodine colour number reaches the value of 5. Three weeks after manufacture, the product had the following properties: refractive index: $n_D^{22} = 1.5034$, the NCO content being 0.2%. FIG. 8 shows the infra-red spectrum, obtained according to Example 8.

EXAMPLE 9

Figure 9:
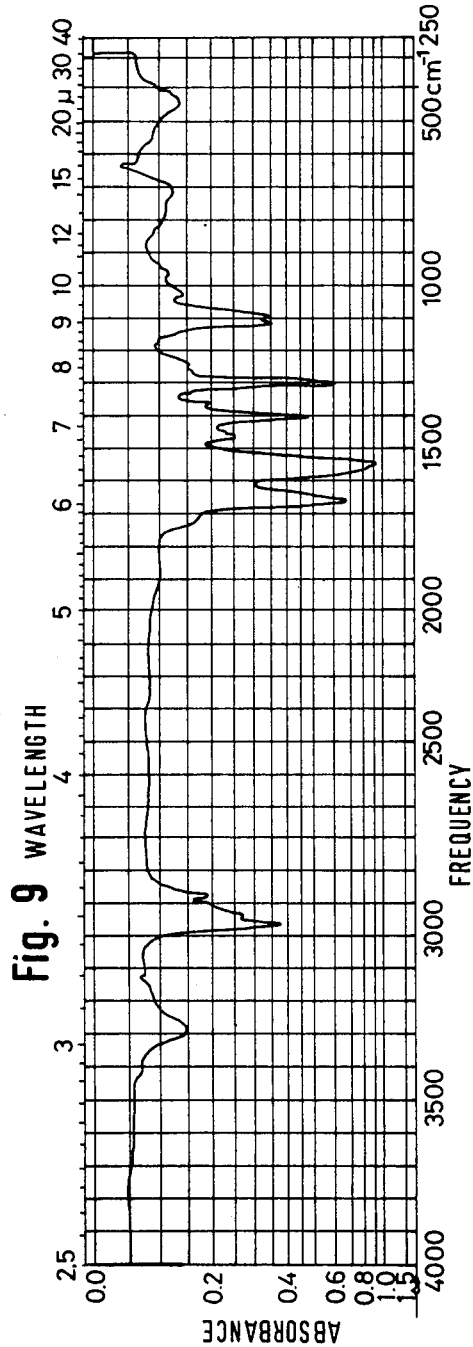

162 g of acetoacetic acid-n-butylester and 0.18 g of zinc acetylacetonate are heated to 90° C whilst stirring and introducing nitrogen, 105 g of 2,2,4-trimethylhexamethylenediisocyanate are uniformly added over the course of 2 hours at 90° C and the reaction is carried out in the course of 5 hours at 90° C. The NCO content is 1.1%. The viscosity is I – J, measured on the Gardner-Holdt scale. The iodine colour number reaches the value of 6. Three weeks after manufacture, the product had the following properties: refractive index: $n_D 22 = 1.5037$, the NCO content being 0.16%. FIG. 9 shows the infra-red spectrum, obtained according to Example 9.

EXAMPLE 10

148 g of acetoacetic acid-iso-propylester and 0.15 g of zinc acetylacetonate are heated to 90° C whilst stirring and introducing nitrogen, 105 g of 2,2,4-trimethylhexamethylenediisocyanate are uniformly added over the course of 2 hours and reacted for 5 hours at 90° C. The NCO content is 1%. The viscosity is U, measured on the Gardner-Holdt scale. The iodine colour number has a value of 6. Three weeks after manufacture, the product had the following properties: refractive index: $n_D 22 = 1.5021$, the NCO content being 0.1%. FIG. 10 shows the infra-red spectrum, obtained according to Example 10.

EXAMPLE 11

148 g of acetoacetic acid-n-propylester and 0.15 g of zinc acetylacetonate are heated to 90° C whilst stirring and introducing nitrogen, 105 g of 2,2,4-trimethylhexamethylenediisocyanate are uniformly added dropwise over the course of 2 hours at the same temperature and reacted over the course of 8 hours at 90° C. The NCO content is 0.9%. The viscosity is L, measured on the Gardner-Holdt scale. The iodine colour number has a value of 5. Three weeks after manufacture, the product had the following properties: refractive index: $n_D 22 = 1.5054$, the NCO content being 0.28%. FIG. 11 shows the infra-red spectrum, obtained according to Example 11.

EXAMPLE 12

162 g of acetoacetic acid sec.-butyl ester and 0.18 g of zinc acetylacetonate are heated to 90° C under nitrogen gas, whilst stirring, 105 g of 2,2,4-trimethylhexamethylenediisocyanate are uniformly added dropwise over the course of 2 hours at the same temperature, and the reaction is carried out for 5 hours at 90° C.

The NCO content is 0.9%. The viscosity is T – U, measured on the Gardner-Holdt scale. The iodine colour number has a value of 5. Three weeks after manufacture, the product had the following properties: refractive index: $n_D^{22} = 1.5025$, with an NCO content of 0.1%. The reaction product obtained has the formula

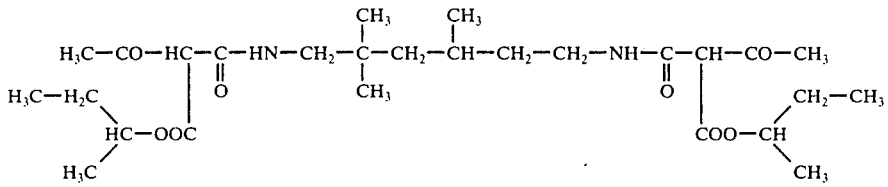

Figure 12:
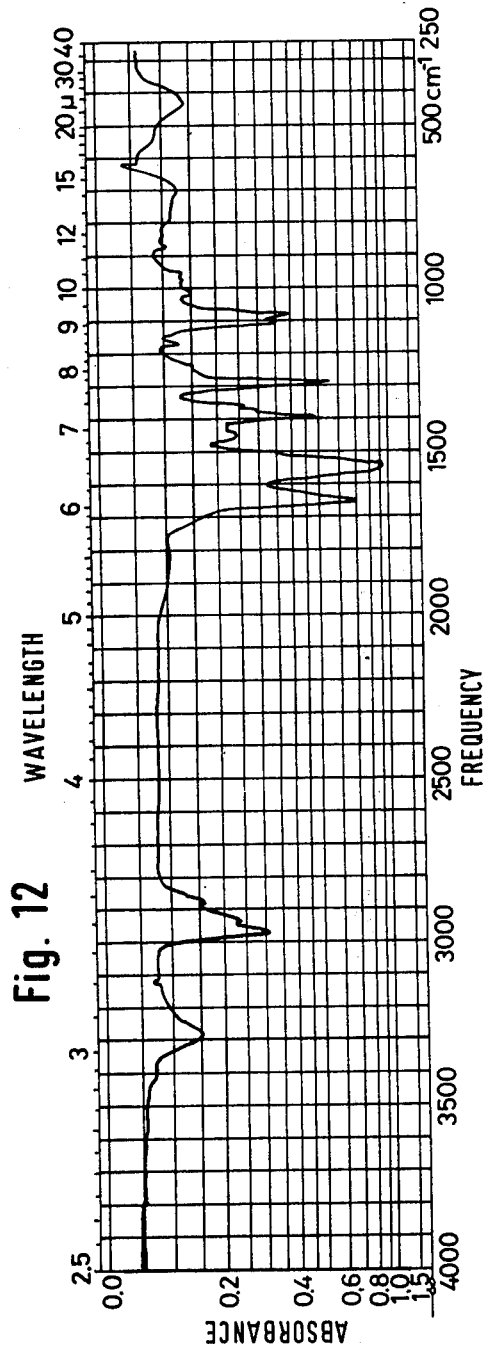

FIG. 12 shows the infra-red spectrum of the reaction product according to Example 12.

EXAMPLE 13

277 g of acetoacetic acid n-dodecyl ester and 0.3 g of zinc acetylacetonate are heated to 90° C under nitrogen, whilst stirring, 105 g of 2,2,4-trimethylhexamethylenediisocyanate are uniformly added dropwise over the course of 2 hours, whilst mainintaining the temperature of 90° C, and the mixture is kept for 2 hours at 90° C.

The NCO content is 0.92%. The viscosity is H – I, measured on the Gardner-Holdt scale. The iodine colour number, measured according to DIN Specification 6162 with a Lovibond 1000 Comparator, is 5.

Three weeks after manufacture, the product had the following refractive index: $n_D^{22} = 1.4883$, the NCO content being 0.14%, this value resulting from storage of the solution for 3 weeks at room temperature.

The reaction product obtained has the formula

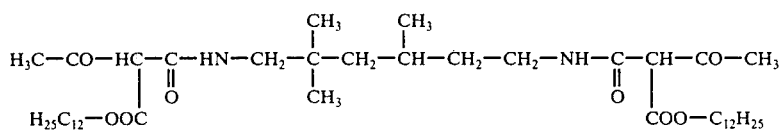

Figure 13:
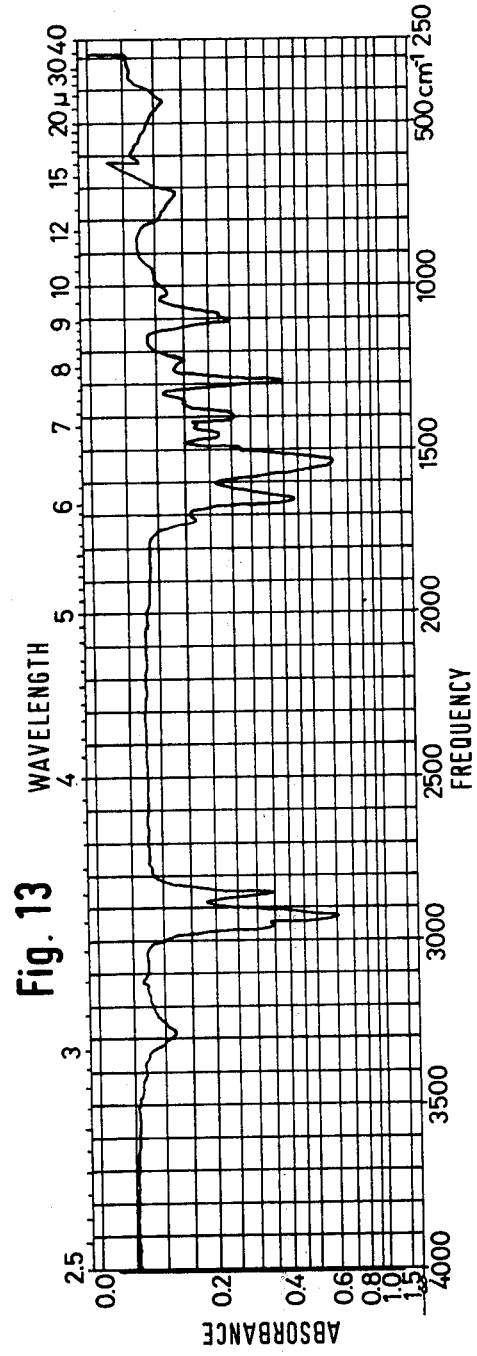

FIG. 13 shows the infra-red spectrum of the reaction product according to Example 13.

EXAMPLE 14

219 g of acetoacetic acid 2-ethylhexyl ester and 0.2 g of zinc acetylacetonate are heated to 90° C under nitrogen gas, whilst stirring, 105 g of 2,2,4-trimethylhexamethylenediisocyanate are uniformly added dropwise over the course of 2 hours at the same temperature, and the reaction is carried out for 3 hours at 90° C.

The NCO content is 0.8%. The viscosity is R, measured on the Gardner-Holdt scale. The iodine colour number has a value of 3.

Three weeks after manufacture, the product had the following properties: refractive index: $n_D^{22} = 1.4990$, the NCO content being 0.11%, this value resulting from storage of the above liquid for 3 weeks at room temperature.

The reaction product obtained has the formula

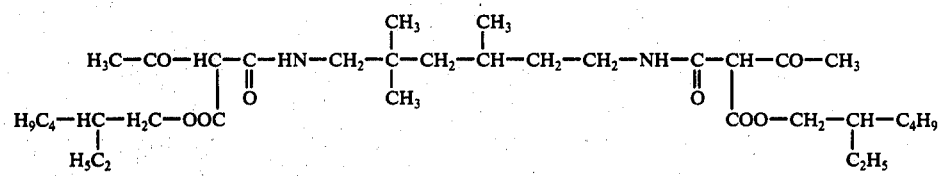

Figure 14:
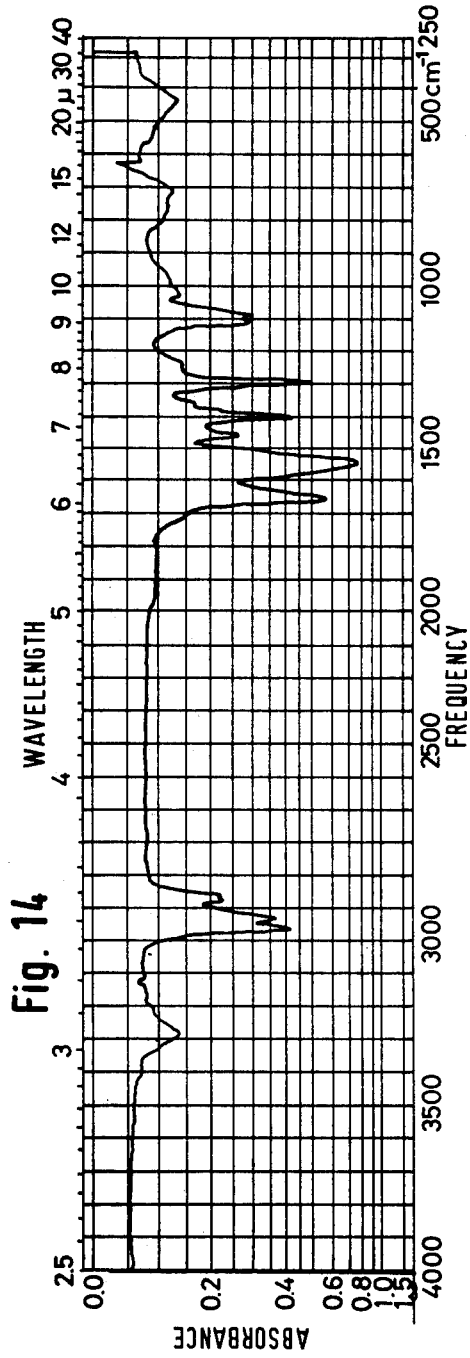

FIG. 14 shows the infra-red spectrum of the reaction product according to Example 14.

EXAMPLE 15

219 g of acetoacetic acid n-octyl ester and 0.2 g of zinc acetylacetonate are heated to 90° C, whilst stirring and introducing nitrogen, 105 g of 2,2,4-trimethylhexamethylenediisocyanate are added uniformly over the course of 2 hours and the reaction is completed in 5 hours at 90° C.

The NCO content is 1.0%. The viscosity is H – I, measured on the Gardner-Holdt scale. The iodine colour number reaches a value of 4.

Three weeks after manufacture, the product had the following properties: refractive index: $n_D^{22} = 1.4955$, the NCO content being 0.15%, this value resulting from storage of the above liquid for 3 weeks at room temperature.

The reaction product obtained has the formula

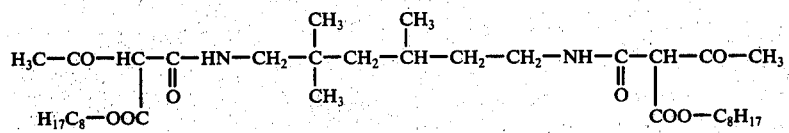

Figure 15:
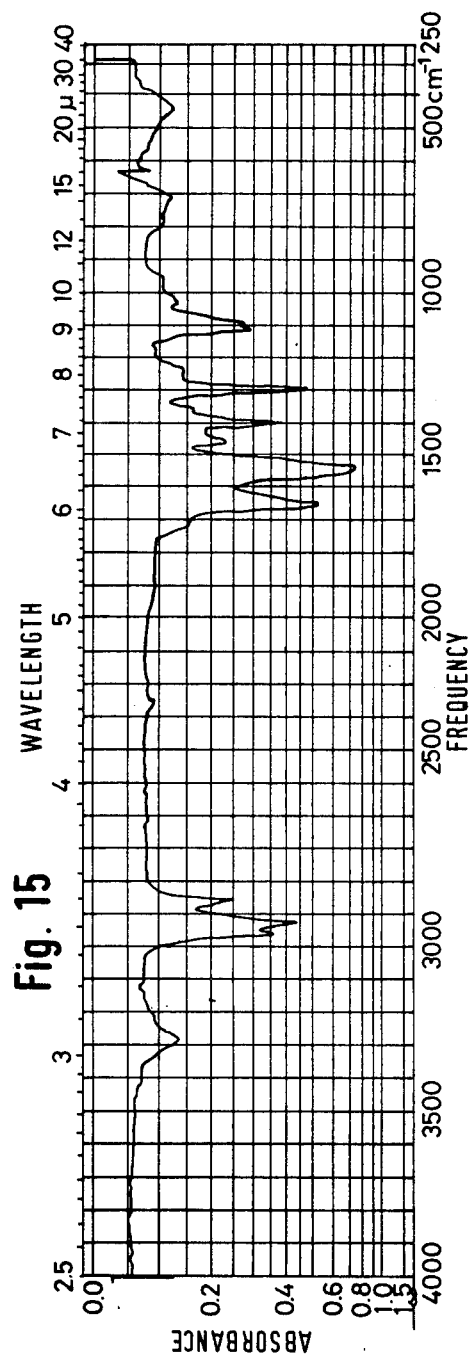

FIG. 15 shows the infra-red spectrum of the reaction product according to Example 15.

EXAMPLE 16

105 g of 2,2,4-trimethylhexamethylenediisocyanate and 0.11 g of zinc acetylacetonate are heated to 75° C under nitrogen gas, whilst stirring, 79 g of acetoacetic acid sec.-butyl ester are uniformly added dropwise over the course of two hours at the same temperature, and the reaction is carried out for 1 hour at 75° C.

The NCO content is 10.5%. The viscosity is G +, measured on the Gardner-Holdt scale. The iodine colour number has a value of 2. Refractive index: $n_D^{22} = 1.4930$, the NCO content being 10.5%.

The reaction product obtained has the formula

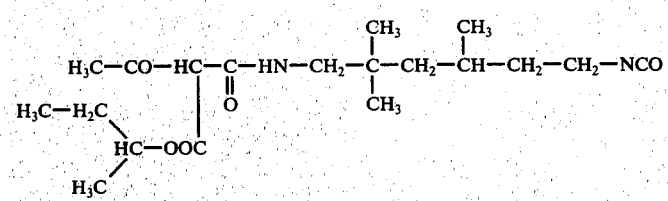

FIG. 16 shows the infra-red spectrum of the reaction product according to Example 16.

EXAMPLE 17

105 g of 2,2,4-trimethylhexamethylenediisocyanate and 0.14 g of zinc acetylacetonate are heated to 75° C under nitrogen, whilst stirring and 135 g of acetoacetic acid n-dodecyl ester are uniformly added dropwise over the course of 2 hours whilst maintaining the temperature of 75° C, and the mixture is kept for 1 hour at 75° C.

The NCO content is 8.36%. The viscosity is D – E, measured on the Gardner-Holdt scale. The iodine colour number, measured according to DIN specification 6162 with a Lovibond 1000 Comparator, is 4. Refractive index: $n_D^{22} = 1.4840$, the NCO content being 8.36%.

The reaction product obtained has the formula

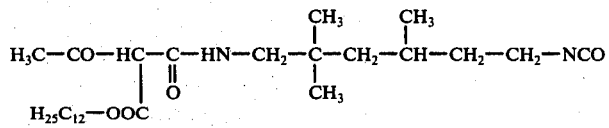

FIG. 17 shows the infra-red spectrum of the reaction product according to Example 17.

EXAMPLE 18

105 g of 2,2,4-trimethylhexamethylenediisocyanate and 0.13 g of zinc acetylacetonate are heated to 75° C under nitrogen gas, whilst stirring, 107 g of acetoacetic acid 2-ethylhexyl ester are uniformly added dropwise over the course of two hours at the same temperature, and the reaction is carried out for 1 hour at 75° C.

The NCO content is 9.02%. The viscosity is H-, measured on the Gardner-Holdt scale. The iodine colour number has the value of 2-3. Refractive index: $n_D^{22} = 1.4913$, the NCO content being 9.02%.

The reaction product obtained has the formula

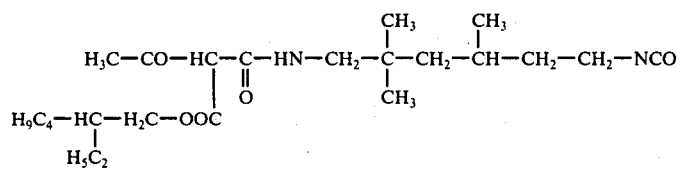

Figure 18:
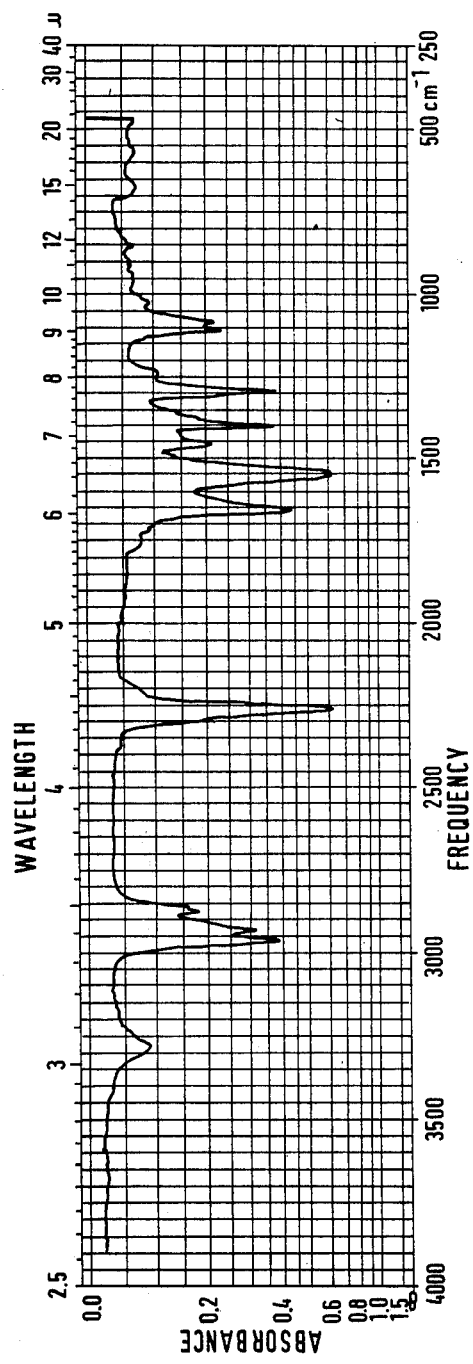

FIG. 18 shows the infra-red spectrum of the reaction product according to Example 18.

EXAMPLE 19

105 g of 2,2,4-trimethylhexamethylenediisocyanate and 0.13 g of zinc acetylacetonate are heated to 75° C, whilst stirring and introducing nitrogen, 107 g of acetoacetic acid n-octyl ester are added uniformly over the course of 2 hours and the reaction is completed in 1 hour at 75° C. The NCO content is 9.69%. The viscosity is B – C, measured on the Gardner-Holdt scale. The iodine colour number reaches a value of 1. Refractive index: $n_D^{22} = 1.4878$, the NCO content being 9.69%.

The reaction product obtained has the formula

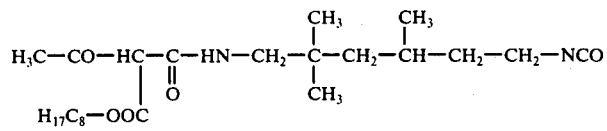

Figure 19:
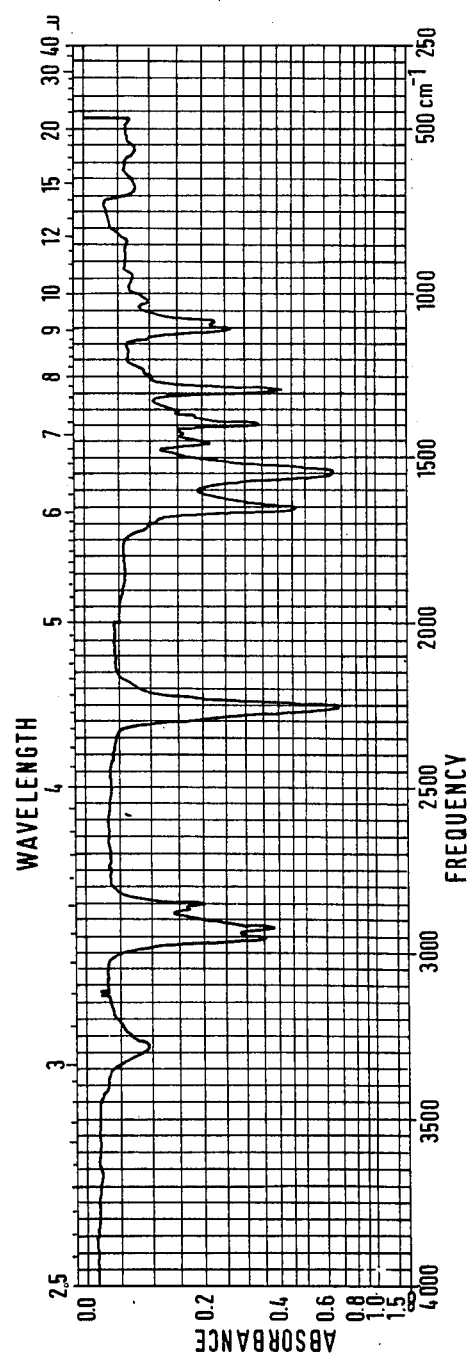

FIG. 19 shows the infra-red spectrum of the reaction product according to Example 19.

EXAMPLE 20

105 g of 2,2,4-trimethylhexamethylenediisocyanate (= 0.5 mol), hereinafter simply described as TMDI, and 0.1 g of zinc acetylacetonate are heated to 75° C in a flask equipped with a stirrer and reflux condenser, and 58 g of acetoacetic acid methyl ester (= 0.5 mol) are added dropwise over the course of two hours at constant temperature. After a reaction time of one hour, an NCO content of 12.9% is obtained. The viscosity of the solution, measured on the Gardner-Holdt scale is B – C at 25° C. The iodine colour number has a value of 1. The refractive index at 22° C has a value of 1.4979.

Figure 20:
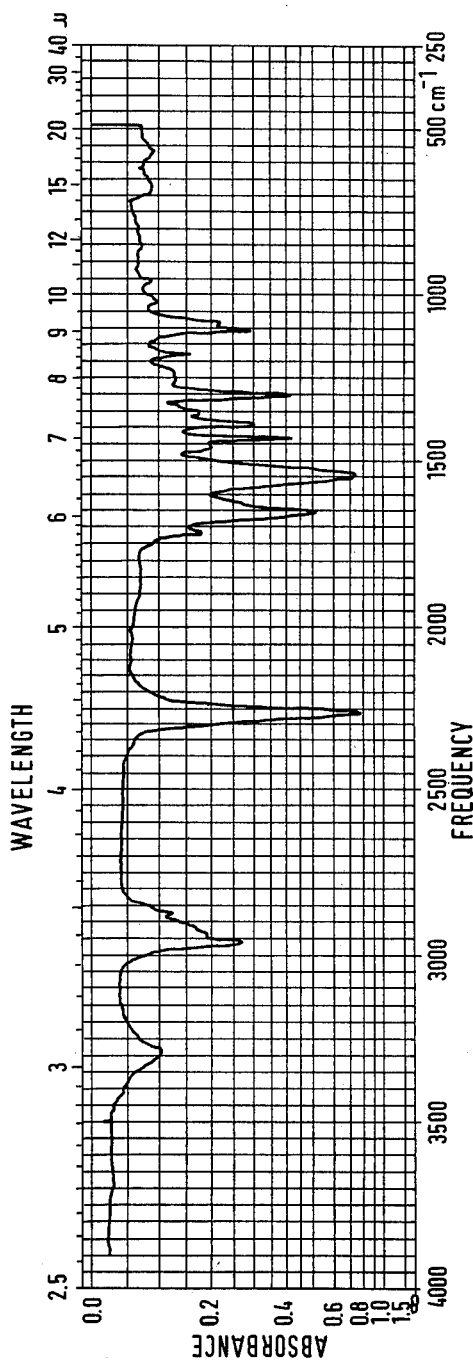
Figure 21:
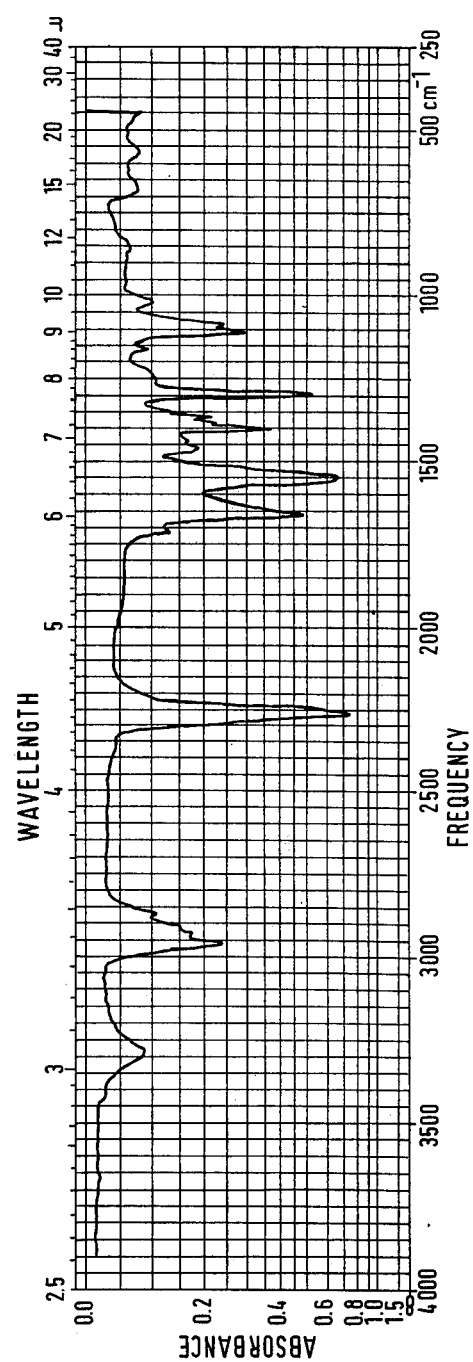
Figure 24:
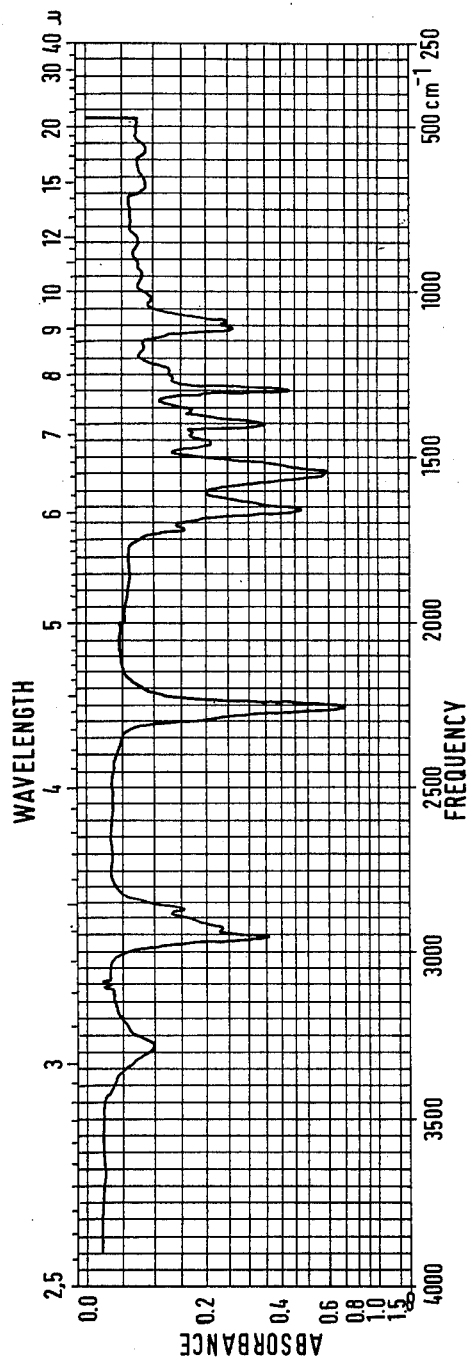
Figure 25:
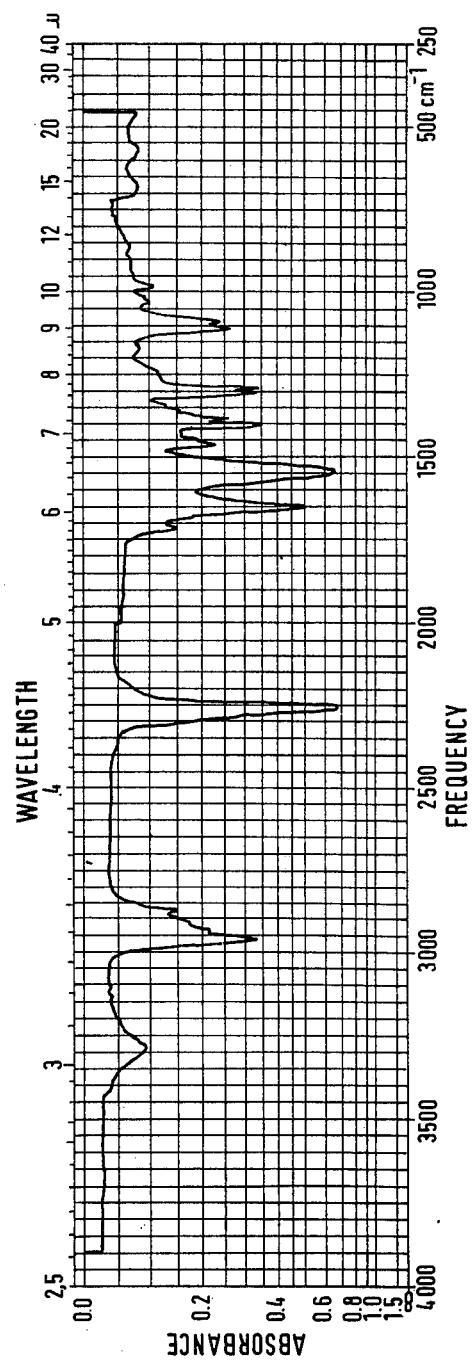
Figure 26:
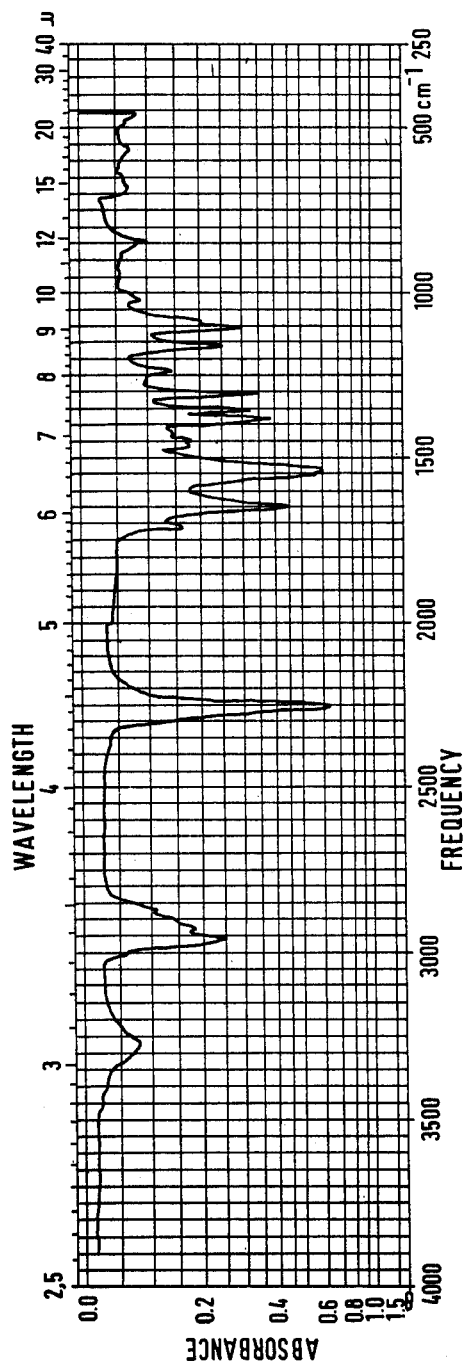
Figure 27:
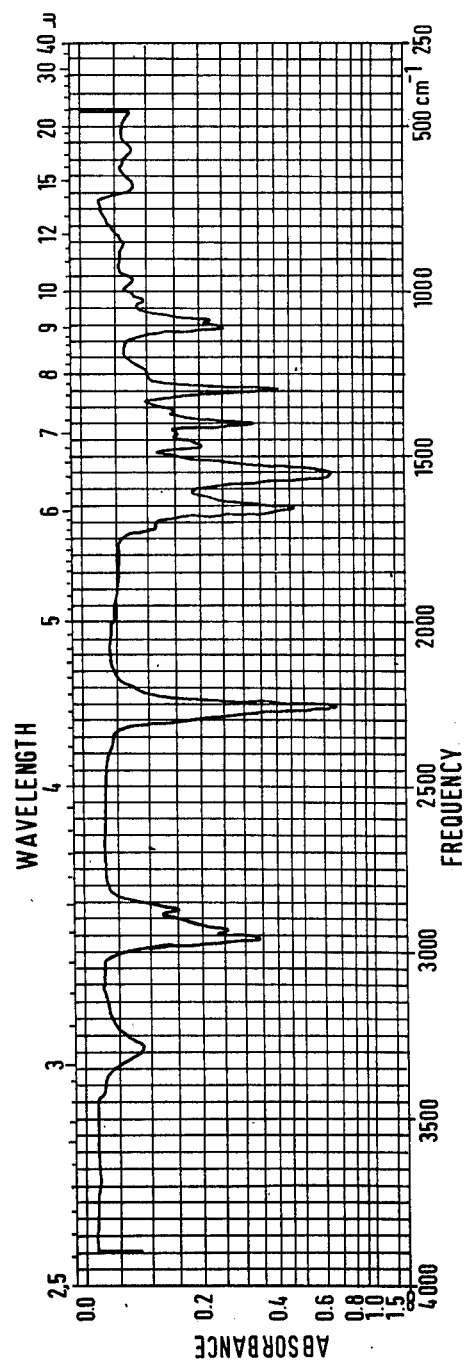
Figure 28:
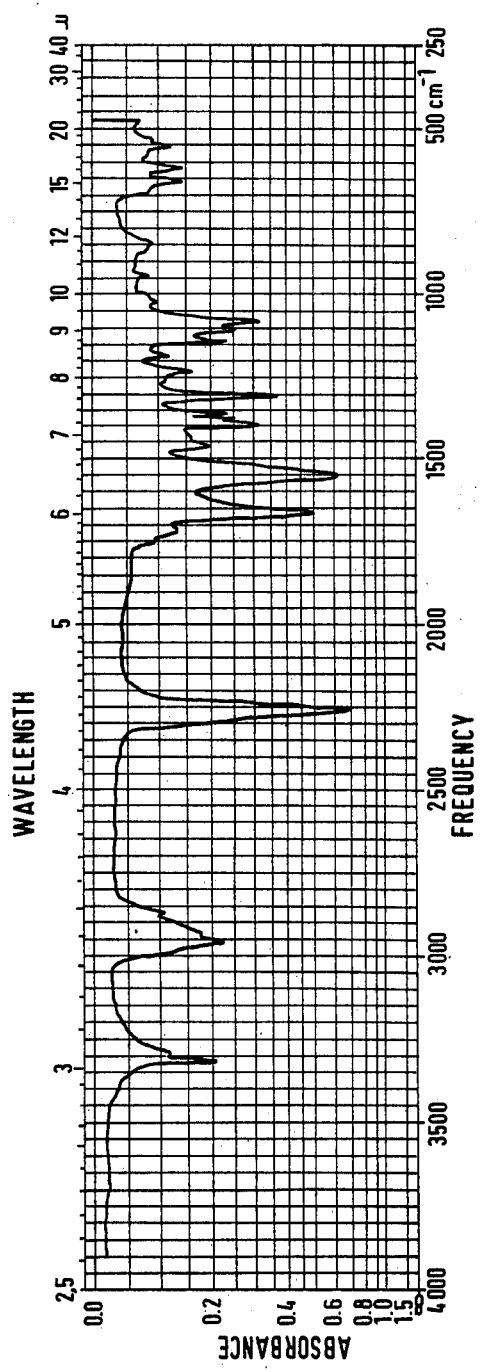

FIG. 20 shows the infra-red spectrum of the reaction product according to Example 20.

The further Examples 21 to 28 are carried out in the same manner so that described in Example 20 (see Table 4 which follows).

EXAMPLE 29

71.2 g of a 50% strength solution of a copolymer, dissolved in xylene, manufactured of 20% by weight of styrene, 20% by weight of hydroxy ethyl methacrylate, 30% by weight of n-butylacrylate and 30% by weight of methyl methacrylate, having a viscosity of V, measured on the Gardner-Holdt scale at 25° C, and 9 g of a partially blocked polyisocyanate consisting of 2,2,4-trimethylhexamethylene diisocyanate and acetoacetic acid-tert.-butyl ester, manufactured according to Example 26, are heated up to 75° C in a flask equipped with a stirrer and a reflux condenser and heated for 25 to 30 minutes. The lacquer-technical results of this reaction product are shown in Table 5.

EXAMPLE 30

71.2 g of a 50% strength solution of a copolymer, dissolved in xylene, manufactured of 20% by weight of styrene, 20% by weight of hydroxy ethyl methacrylate, 30% by weight of n-butylacrylate and 30% by weight of methyl methacrylate, having a viscosity of V, measured on the Gardner-Holdt scale, at 25° C, and 9 g of a partially blocked polyisocyanate consisting of 2,2,4-trimethylhexamethylenediisocyanate and acetoacetic acid-tert.-butyl ester, manufactured according to Example 21, are heated up to 75° C in a flask equipped with a stirrer and a reflux condenser and heated for 25 to 30 minutes. The lacquer-technical results of this reaction product are shown in Table 5.

Table 5

| Stoved coatings with a dry film thickness of 90 μ | | | | |
|---|---|---|---|---|
| | Example 29 according to the invention | | Example 30 according to the invention | |
| | Stoving conditions after 40 minutes at | | Stoving conditions after 40 minutes at | |
| | 130° C | 150° C | 130° C | 150° C |
| Konig pendulum hardness in sec. | 200 | 205 | 205 | 210 |
| Elasticity, assessment as film split | 1 | 1 | 1-2 | 1-2 |
| Resistance to xylene after six minutes | 2 | 1-2 | 2 | 1-2 |

Assessment of stoved coatings:
1 = best value,
5 = worst value

The reaction of the partially blocked polyisocyanates with hydroxyl groups containing polymers and hydroxyl groups containing synthetic resins, respectively, happens in the wide range of temperature from 30° to 100° C, whereby the condensation times in the low range of temperature can amount from 30° to 50° C over the course of several hours, whilst up to 60° to 100° C the reaction time must be reduced from 60 to about 15 minutes in order to obtain gel free products.

The mixture ratio amounts to 5 to 50% by weight of the reaction products consisting of 2,2,4-trimethylhexamethylenediisocyanate and acetoacetic acid alkyl esters according to the invention and 50 to 95% by weight of hydroxyl groups containing synthetic resins. The mixture ratio comprises the further demand that 0.3 to 1.2 NCO groups in the form of partially blocked isocyanate groups are to be insisted for one hydroxyl group.

Table 4

Partially blocked polyisocyanates obtained from 2,2,4-trimethylhexamethylenediisocyanate and acetoacetic acid alkyl esters.

| Example | TMDI 0.5 mol | Acetoacetic acid alkyl ester 0.5 mol | Catalyst Zinc acetyl-acetonate | NCO content after reaction, in % | Iodine colour number | Viscosity of the solution+ | Refractive index at 22° C |
|---|---|---|---|---|---|---|---|
| 21 | 105 g | 65 g of acetoacetic acid ethyl ester | 0.1 g | 11.9 | 2 | B - C | 1.4950 |
| 22 | 105 g | 72 g of acetoacetic acid n-propyl ester | 0.11 g | 11.1 | 3 | C | 1.4935 |
| 23 | 105 g | 72 g of acetoacetic acid iso-propyl ester | 0.11 g | 10.9 | 2 | E - F | 1.4921 |
| 24 | 105 g | 79 g of acetoacetic acid n-butyl ester | 0.11 g | 10.7 | 2 | C | 1.4941 |
| 25 | 105 g | 79 g of acetoacetic acid iso-butyl ester | 0.11 g | 10.8 | 2 | E - F | 1.4924 |
| 26 | 105 g | 79 g of acetoacetic acid tert.-butyl ester | 0.11 g | 10.4 | 2-3 | T - U | 1.4890 |
| 27 | 105 g | 86 g of acetoacetic acid n-amyl ester++ | 0.11 g | 10.5 | 2 | B - C | 1.4912 |
| 28 | 105 g | 86 g of acetoacetic acid tert.-amyl ester++ | 0.11 g | 10.1 | 6 | X | 1.4992 |

+measured on the Gardner-Holdt scale at 25° C
++referred to as pentyl radicals in the description
FIG. 21 to FIG. 28 show the infrared spectrum of the reaction product according to Ex. 21-28.

What is claimed is:

1. A compound of the formula

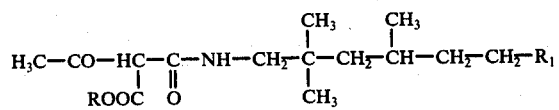

wherein $R_1$ denotes -NCO or the radical

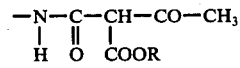

and each R denotes a radical selected from the group consisting of methyl, ethyl, propyl, isopropyl, n-butyl, tert-butyl, isobutyl, sec-butyl, pentyl, hexyl, heptyl, octyl, nonyl, decyl, and dodecyl radical.

2. A compound according to claim 1, wherein $R_1$ denotes -NCO and R is tert-butyl.

* * * * *

UNITED STATES PATENT OFFICE
CERTIFICATE OF CORRECTION

Patent No. 4,068,086  Dated Jan. 10, 1978

Inventor(s) Horst Dalibor

It is certified that error appears in the above-identified patent and that said Letters Patent are hereby corrected as shown below:

[30], last line: "2628/75" should read --2628/76--

Col. 3, line 15: "
$$CH_2 - \underset{\underset{CH_3}{|}}{\overset{\overset{CH_3}{|}}{C}} - CH_2 - \overset{CH_3}{CH}$$
"

should read $$-- CH_2 - \underset{\underset{CH_3}{|}}{\overset{\overset{CH_3}{|}}{C}} - CH_2 - \overset{CH_3}{CH} --$$

Signed and Sealed this

*Thirteenth* Day of *June 1978*

[SEAL]

*Attest:*

RUTH C. MASON
*Attesting Officer*

DONALD W. BANNER
*Commissioner of Patents and Trademarks*